United States Patent [19]

Hendrickson et al.

[11] Patent Number: 4,855,234

[45] Date of Patent: * Aug. 8, 1989

[54] BIOLOGICALLY ACTIVE PROTEIN IMMOBILIZED WITH A POLYMERIC FIBROUS SUPPORT

[75] Inventors: Carol E. Hendrickson, St. Joseph Township, Ramsey County, Wis.; Rosa Uy; Arlene J. Mencke, both of St. Paul, Minn.

[73] Assignee: Minnesota Mining and Manufacturing Company, St. Paul, Minn.

[ * ] Notice: The portion of the term of this patent subsequent to Jul. 12, 2005 has been disclaimed.

[21] Appl. No.: 169,832

[22] Filed: Mar. 17, 1988

Related U.S. Application Data

[63] Continuation of Ser. No. 796,274, Nov. 8, 1985, Pat. No. 4,757,014.

[51] Int. Cl.$^4$ .................... C12N 11/06; C12N 11/02; C12N 11/08
[52] U.S. Cl. ..................... 435/181; 435/177; 435/180
[58] Field of Search ............... 435/174, 176, 177, 180, 435/181, 182

[56] References Cited

U.S. PATENT DOCUMENTS

| | | | |
|---|---|---|---|
| 3,282,702 | 11/1966 | Schreibner | 99/54 |
| 3,715,278 | 2/1973 | Miller | 195/63 |
| 3,928,143 | 12/1975 | Coughlin | 435/176 X |
| 4,038,485 | 7/1977 | Johnston et al. | 23/230 B |
| 4,098,645 | 7/1978 | Hartdegen et al. | 195/68 |
| 4,115,198 | 9/1978 | Coughlin et al. | 435/176 |
| 4,118,536 | 10/1978 | Beardsley et al. | 528/23 X |
| 4,210,722 | 7/1980 | Silver | 435/176 |
| 4,258,133 | 3/1981 | Mirabel et al. | 435/176 |
| 4,448,884 | 5/1984 | Henderson | 435/176 X |
| 4,473,550 | 9/1984 | Rosenbaum et al. | 424/94 |
| 4,564,532 | 11/1986 | Henderson | 435/176 X |
| 4,585,488 | 4/1986 | Giefer | 134/27 |
| 4,588,586 | 5/1986 | Kessler et al. | 424/94 |
| 4,748,992 | 6/1988 | Giefer | 134/84 |
| 4,757,014 | 7/1988 | Hendrickson et al. | 435/180 |

FOREIGN PATENT DOCUMENTS

| | | |
|---|---|---|
| A6065286 | 7/1986 | Australia . |
| 0082798 | 6/1983 | European Pat. Off. . |
| 0155505 | 9/1985 | European Pat. Off. . |
| 0209071 | 1/1987 | European Pat. Off. . |
| 8607264 | 12/1986 | PCT Int'l Appl. . |

*Primary Examiner*—David M. Naff
*Attorney, Agent, or Firm*—Donald M. Sell; Walter N. Kirn; Lorraine R. Sherman

[57] ABSTRACT

A composite article is prepared having in sequence a fibrous support which has been subjected to a surface treatment to provide binding sites thereon, a layer of a protein immobilizer compound, and a biologically active protein such as enzyme. The surface treatment can be carried out by coating the surface with an inorganic oxide or by subjecting the surface to plasma treatment.

9 Claims, No Drawings

BIOLOGICALLY ACTIVE PROTEIN IMMOBILIZED WITH A POLYMERIC FIBROUS SUPPORT

This is a continuation of application Ser. No. 06/796,274 filed Nov. 8, 1985 now U.S. Pat. No. 4,757,014.

FIELD OF THE INVENTION

This invention relates to a composite article comprising an immobilized biologically active protein. In another aspect, a process for preparing the composite article of the invention is disclosed. The article can be used in a method for disinfecting medical devices, particularly contact lenses.

BACKGROUND OF THE INVENTION

Soft contact lenses, such as those made from plastic gel materials, e.g., hydroxyethyl methacrylate (HEMA) or its analogues and ethylene glycol dimethacrylate (EGMA) of its analogues, are replacing traditional hard contact lenses as the lenses of choice for many people. Soft lenses are more comfortable to wear than the hard lenses, but they pose a more complex problem than the hard lenses when it comes to care and maintenance. Hard lenses may be cleaned and disinfected relatively easily. Since they do not absorb appreciable amounts of water and aqueous solutions, the use of somewhat harsh cleaning and disinfecting agents is not generally a problem.

Soft lenses, on the other hand, require greater care in cleansing and storage. The solutions useful with hard lenses often are not compatible with soft lenses because the soft lenses tend to absorb or concentrate certain constituents of the formulation, which could result in damage to the lens or harm to the eye of the user.

Similarly, soft lenses are more vulnerable to microbial contamination than are hard lenses. the nutritive effect of body fluids, and the protective effect of nicks or imperfections in soft lenses, can serve to augment the growth of microbes.

While it is relatively easy to find antimicrobial agents active against such microbial contaminants, it is more difficult to find an antimicrobial agent that is compatible with soft contact lenses, and more difficult yet to find one that is non-irritating and safe for contact with the human eye.

Antimicrobial agents which are suitable for external contact or even for injection or ingestion are often unsuitable for use in eye care due to the particularly sensitive nature of the tissues in the eye. For example, they might be unsuitable because of direct toxicity to the eye, poor solubility in aqueous vehicles, eye irritation or ocular allergenic effects, absorption or binding by the contact lens, or chemical interaction with the contact lens or even its plastic lens case.

An antimicrobial agent useful for ocular applications must not contribute to any of the above problems. In particular, it must satisfy two basic requirements, i.e. that it be non-irritating to the eye, and that it be effective against a wide variety of microorganisms.

Hydrogen peroxide is a very effective antimicrobial agent which is currently used to disinfect contact lenses, including soft contact lenses. Although it is potentially irritating to the eye if significant residues are contained on or in the contact lens, it is known that hydrogen peroxide can be removed by soaking a disinfected lens in a solution containing a catalyst such as platinum oxide which catalyzes the decomposition of hydrogen peroxide.

Solutions of the enzyme catalase have also been added to decompose hydrogen peroxide in solutions previously used to sterilize contact lenses. See, for example, European Patent application 82710055.3. However, if introduced into a solution with a lens, catalase can bind to the lens, compounding the familiar protein deposit problem associated with the use of contact lenses.

It is known in the art that certain proteins can be immobilized on specific supports. U.S. Pat. No. 4,098,645 describes the immobilization of enzymes on isocyanate end-capped polyurethane polymer foams, and catalase is one of a long list of enzymes listed and claimed.

U.S. Pat. No. 3,282,702 describes certain classes of polymeric carriers which bind catalase for the purpose of providing articles for removing hydrogen peroxide from potable liquids.

U.S. Pat. No. 4,210,722 describes a method of immobilizing a protein such as an enzyme on a polar support in a variety of configurations which can be glass, ceramic, inorganic oxide, etc. comprising applying a layer of a polymer having repeatig units containing a beta-hydroxyalkyleneamine moiety such as the dimethylamine adduct of epoxidized polybutadiene to a polar support and contacting the treated support with an aqueous solution of the protein. One of the enzymes exemplified in this patent is catalase.

SUMMARY OF THE INVENTION

Briefly, the present invention provides a composite article comprising in sequence a fibrous support which has been subjected to a surface modification treatment to provide binding sites thereon, a layer of protein immobilizer, and a biologically active protein.

In another aspect, a process for preparing composite articles containing immobilized protein is disclosed.

Fibrous supports, such as woven and particularly nonwoven webs, because of their ease of handling and high surface area, provide desirable constructions upon which proteins such as enzymes can be immobilized. It has been found, however, that some of the typical polymers used to make woven and nonwoven webs, such as polyalkylenes, do not irreversibly absorb or bind the protein immobilizers known to the art. Immobilized proteins such as enzymes can retain a substantial portion of their biological activity even though bound to a support.

Surprisingly, it has been found that certain polymers, including polyalkylenes, commonly used to make nonwoven webs can be used as supports for protein immobilization if their surface is first subjected to a modification treatment capable of providing binding sites for a protein immobilizer compound. It has not previously been known to treat woven and nonwoven webs for the purpose of providing binding sites for chemical additives.

It has not previously been known that it is possible to achieve disinfection with hydrogen peroxide while simultaneously decomposiing excess hydrogen peroxide by the use of the protein catalase immobilzed upon a support. In particular, the use of catalase, immobilized upon a woven or nonwoven fibrous support coated with a layer of inorganic oxide or subjected to a plasma treatment, to decompose hydrogen peroxide has not been known.

Hydrogen peroxide systems, which have been used to disinfect contact lenses, may be classified by the number of containers used during the disinfection process and by the number of steps required to complete the disinfection process.

A two-container, two-step method involves separate, noncompeting reactions. In the first step lenses are put into a container containing an amount of hydrogen peroxide sufficient for disinfecting the lenses in a short period of time (about 10 minutes). In the second step, as is known in the art, the lenses are then transferred to a second container which contains a saline solution and a disc of platinum. The platinum disc catalytically converts the hydrogen peroxide into molecular oxygen and water. The lenses are soaked in the second container for four or more hours to remove the residual hydrogen peroxide from the lenses. Other systems which have been used to remove the hydrogen peroxide from the lenses can include either the use of a solution of sodium bicarbonate or the enzyme catalase in solution. These systems may use one or two containers but always require two steps: first a soak in hydrogen peroxide and second a neutralization step.

The two-step, two-container system is bulky, cumbersome and requires relatively large volumes of solutions. Two-step, one-container systems are also bulky, cumbersome and require more than one solution. A problem arises when the wearer forgets the second step and does not neutralize the hydrogen peroxide in the lenses. The wearer then has lenses which are contaminated with hydrogen peroxide and are not suitable for use. It is, therefore, desirable to provide a system which uses only one container and one step to achieve the disinfection of the lenses and the neutralization of the hydrogen peroxide.

When a one-step system is used to disinfect contact lenses there are two competing reactions which must be controlled to achieve disinfection as well as neutralization. One reaction is the killing of the infectious organisms on the lenses by the hydrogen peroxide. The concentration of the hydrogen peroxide must remain at a high enough level for a period of time long enough to achieve disinfection. The second reaction is the conversion of residual hydrogen peroxide into water and molecular oxygen or other compounds. The conversion reaction must be slow enough to allow killing of the microorganisms but fast enough to neutralize substantially all of the hydrogen peroxide in a period of time suitable for having the lenses ready for use (usually four to six hours).

The present invention permits the use of a onecontainer, one-step system by controlling the amount of enzyme present. The amount of immobilized enzyme put into the container can be controlled by selecting the appropriate amount of composite article. A low amount of enzyme will cause a slow neutralization of hydrogen peroxide which will allow the disinfection to take place. If, on the other hand, a fast system for hydrogen peroxide disinfection is desired, a two-step system would be preferable: a large concentration of enzyme can be put into the container after the 10-minute disinfecting soak and the large amount of enzyme will neutralize the hydrogen peroxide very rapidly, reducing the total required time for disinfection. A very fast system is highly desirable for patients wearing extended wear lenses who do not wish to leave their lenses out of their eyes for the four- to six-hour period required by products currently available.

The activity of the enzyme in neutralizing hydrogen peroxide can also be attentuated by use of controlled release technology, as is known in the art. For example, the composite article of the invention may be coated with a slowly erodable polymer such as a cellulose derivative, poly(N-vinyl pyrrolidone) or poly(vinyl alcohol). The erodable polymer coating on the surface prevents the enzyme from neutralizing the hydrogen peroxide and slowly dissolves in the hydrogen peroxide solution. When the polymeric coating has dissolved into the solution, the enzyme neutralizes the hydrogen peroxide at a rate proportional to the amount of active enzyme present.

The medical devices which can be disinfected in conjunction with the composite article of the invention can be any article which is used in or applied to the human body and which must be free of significant amounts of hydrogen peroxide after disinfection. Such articles include devices used in the eye which may require regular disinfection such as contact lenses. Other articles suitable for disinfection include medical and dental instruments, surgical staples, and implants of various types. A method for disinfecting medical devices using the article of the invention is disclosed in assignee's copending patent application U.S. Ser. No. 06/796272, filed the same date as this application.

As used in this application:

"woven fibrous web" means a sheet or pad of interlaced strands of yarn;

"nonwoven fibrous web" means a sheet or pad of a random network of fibers;

"ceramic" means any inorganic nonmetallic material (includes metal and nonmetallic oxides) which requires the application of high temperatures at some stage in its manufacture but is not derived from a melt;

"ceramic-precursor" means a material capable of being converted to a ceramic by application of high temperature;

"sol" means a colloidal dispersion of a finely divided solid phase in a liquid medium;

"polar layer" means a layer the surface of which is wettable by water;

"continuous" means a layer with virtually no discontinuities or gaps therein;

"gelled network" means an aggregation of colloidal particles linked together to form a porous three-dimensional network;

"particle" means spherical, non-spherical, and fibrillar particulate arrangements;

"primary particle size" means the average size of unagglomerated single particles of inorganic metal oxide;

"porous" means the presence of voids created by the packing of particles; the dried product preferably has an open porosity of between 25 and 70 percent;

"monolayer" means a thin layer approximately 10 to 250 angstroms thick, with the preferred thickness being in the range of 10 to 100 angstroms;

"mat" means unfused fiber;

"thermally bonded" means a mat of fibers that has been fused by heat at junction points (e.g., passed through calendering rolls at 232° C. (450° F.)); and "embossing" means a mat of fibers thermally fused by imprinting a pattern on the mat.

DETAILED DESCRIPTION OF THE INVENTION

The present invention provides a composite article comprising in sequence:

(a) a woven or nonwoven fibrous support which has been subjected to a surface modification treatment selected from the group consisting of:
 (1) a gelled network of inorganic oxide particles which, preferably, is a layer of a porous ceramic-precursor gel, and
 (2) a plasma treatment,
(b) a layer of a protein immobilizer compound, and
(c) a biologically active protein, such as catalase.

For many uses it is desirable for a protein, once it has been immobilized on a support by means of a protein immobilizer, to be retained in its entirety or substantially in its entirety on the support so as to not contaminate another substance. It has been found that binding of a protein immobilzer to the support is enhanced when the support is provided with polar groups. Polar groups provide binding sites which can then interact with the protein immobilzer. Such binding sites allow binding of the protein immobilizer to be maximized. The protein to be immobilized can then be firmly attached to the support for its intended utility.

Woven and nonwoven webs are useful as supports for the articles of the invention. Fibrous webs are desirable for use in the method of the invention because they provide large surface areas for binding protein. Woven webs are alternatives to nonwoven webs for the purposes of the invention. A wide variety of fiber diameters, e.g., 0.05 micrometers in to 50 micrometer diameter, preferably 0.1 to 20 micrometers, can be used as the support in the composite articles of the invention. Any web thickness can be useful in specific applications, preferably 0.2 micrometer to 100 cm thick, most preferably 0.1 mm to 1 cm. In applications such as filtration, chromatography, or plasmaphoresis, web thicknesses of 50 and even 100 cm or more can be useful.

Nonwoven fibrous webs are preferred in the practice of the invention. Nonwoven webs have several advantages over woven maerials including high surface area, ease of manufacture, low material cost, and allowance for variation in fiber texture and fiber density.

The preferred materials useful to prepare nonwoven fibrous web compositions of the invention include polymers and copolymers of monomers which form fibrous webs. Suitable polymers include polyalkylenes such as polyethylene and polypropylene, polyvinyl chloride, polyamides such as the various nylons, polystyrene, polyarylsulfones, polyvinyl alcohol, polyacrylates such as polymethyl methacrylate, polycarbonate, cellulosics such as cellulose acetate butyrate, polyesters such as poly(ethylene terephthalate), polyimdes, and polyurethanes such as polyether polyurethanes, and combinations thereof. Nonwoven webs may also be prepared from combinations of co-extruded polymers such as polyester and polyalkylenes. Copolymers of the monomers which provide the above-described polymers are also included within the scope of the invention. Nonwoven webs may also be combined webs which are in intimate blend of fine fibers and crimped staple fibers.

Fibrous webs of the invention can be prepared by methods known in the art. Nonwoven form webs may be prepared by melt-blowing as is known to those skilled in the art and disclosed in, for example, U.S. Pat. No. 3,978,185 and in V. A. Wente et al. "Manufacture of Superfine Organic Fibers", Naval Research Laboratories Report No. 4364, Navel Research Laboratories, Washington, D.C. (U.S. Document No. 111437) which are incorporated herein by reference. Alternative techniques such as solution-blowing can also be used as described, for example, in U.S. Pat. No. 2,571,457, which is incorporated herein by reference. The method used to prepare the unwoven material is not critical.

Nonwoven webs can be embossed or thermally bonded, as is known in the art, to give integrity to the web. Pillowing of nonwovens can be useful and is described in detail in U.S. Pat. Nos. 4,042,740 and 4,103,058. The nonwovens of these patents are useful in the present invention. Woven fibrous webs include any type of patterned or knitted fabric or pad.

In one embodiment, the fibrous support can be coated on one or more surfaces with a layer of an inorganic oxide capable of providing binding sites to the support surface. Such materials are wettable by water and include metal oxides, glasses, ceramic precursors, and clays. Silaceous materials such as sand, glass and quartz are generally suitable. Inorganic compounds such as oxides and barium ferrite are also considered suitable. Preferred material are inorganic oxides which form gelled networks. Most preferably the polar layer is a continuous, porous ceramic-precursor gel layer consisting of spherical particles preferably of 20 to 600 angstroms and most preferably of about 50 angstroms in diameter. These gels are preferred because they are found to bond readily to nonwoven webs. The amount of gel used will generally be about 0.06 to 0.15 grams per gram of nonwoven web.

The layer of inorganic oxide is substantially uniform in thickness and is substantially permanently adhered to the support, i.e. has a 180° peelback value of at least about 150 g/cm, preferably at least about 500 g/cm (as measured on polyester (PET) film). The dried coating is preferably from about 2 to 500 nm thick. Such coatings provide good adhesion. When the coating thickness is too great, the coating has reduced adhesion and flexibility and may flake off or form powder under mechanical stress.

In another embodiment, a plasma treatment utilizing an activated gas such as air, oxygen, carbon dioxide, argon, helium, nitrous oxide, water vapor, and the like, and combinations thereof, can be utilized as an alternative to a layer of inorganic oxide material, to provide a water-wettable or polar surface on the support. These treatments are alternatives to use of a layer of polar material coated on the support.

Protein immobilizers useful in the method of the invention are any of the known polymers which adhere readily to polar supports and provide immobilization of proteins, such as enzymes, while preferably retaining substantially all of the biological activity of the protein.

Included among the suitable protein immobilizers and/or coupling agents are polymers having repeating units containing a beta-hydroxyalkyleneamine moiety, silanefunctional compounds such as gamma-aminopropyltriethoxysilane and silane-treated polycarbodiimide polymers of U.S. Pat. No. 4,118,536.

It is presently preferred to use polymers such as those described in U.S. Pat. No. 4,210,722, the teaching of which patent is incorporated herein by reference. The polymers described as useful in that invention are generally useful in the present invention. A particularly preferred type of polymer described in the above patent is N,N-dialkylamine adducts of epoxidized polybutadiene such as the N,N-dimethylamine adduct of epoxidized polybutadiene. Although this reference discloses only water-soluble protein immobilizers, the present invention includes within its scope both water-soluble and organic solvent-soluble (e.g., toluene) protein immobilizes.

Especially preferred polymers for practicing the invention are formed from amine adducts of epoxidized poly-cis-1,4-butadiene, epoxidized styrene/cis-1,4-butadiene, and polyglycidyl methacrylate wherein the amine can be a primary or secondary amine such as dimethylamine, diethylamine, morpholine, piperidine, or n-propylamine, as described in U.S. Pat. No. 4,210,722.

The β-hydroxyalkyleneamine-containing polymers have molecular weights ranging from 1000 to several million. However, the preferred molecular weight is in the range of 10,000 to 250,000. As the molecular weight is increased above about 250,000, the aminated polymers create preparative problems.

Enzymes immobilized by, for example, β-hydroxyalkyleneamine-coated fibrous supports as described herein, are useful in enzymatic chemical processing in the conventional manner. Examples thereof include the use of glucose isomerase in the conversion of glucose to fructose, and the use of lactase in the removal of lactose during the isolation of proteins from cheese whey. Further examples of enzymes which can be strongly attached, for example, to the β-hydroxyalkyleneamine polymers include urease, glucose oxidase, invertase, catalase, peroxidase, papain, lipase, cellulase, dextranase, amylase, ribonuclease, carboxypeptidase and urokinase.

Immunochemicals such as antigens and antibodies may be conveniently attached to supports according to the invention and used in a conventional manner.

Examples of immunologically-active proteins which may be immobilized according to the invention include gamma globulins, haptoglobin, $\alpha_1$-antitrypsin inhibitor, serum albumin transferrin, complement and $\alpha$-globins.

The process of the invention in one embodiment comprises coating woven or nonwoven webs with a polar compound from a solution or sol containing inorganic oxide particles, the particles preferably having an average primary particle size less than about 200 angstroms (A), more preferably less than about 70 A. The solution preferably contains 0.2 to 15, preferably 0.5 to 6, weight percent of the particles. At particle concentrations above 15 weight percent, the resulting coating may have reduced uniformity in thickness and exhibit reduced adhesion to the support surface. At concentrations below 0.2 weight percent, process inefficiencies result due to the large amount of liquid which must be removed.

It is preferred to use sols of inorganic oxides, particularly sols of ceramic-precursor materials as the polar compound used to coat the fibrous supports. Inorganic oxides particularly suitable for use in the present invention include colloidal silica particles, boehmite (alpha-$Al_2O_3 \cdot H_2O$), tin oxide ($SnO_2$), antimony oxide ($Sb_2O_5$), zirconium oxide ($ZrO_2$), and alumina-coated silica as well as other inorganic oxides of Groups III and IV of the Periodic table and mixtures thereof. The selection of the inorganic oxide depends upon its ability to adhere to the support and provide adequate binding for the protein immobilizer compound.

Examples of commercially available inorganic metal oxides include colloidal silica sols (Nalco TM 2326 and Nalco TM 1034A, Nalco Chemical Co., Oal Brook, IL), dispersable alumina boehmite (Dispural TM and Pural TM, Condea Petrochemie GmbH, and Catapal SB TM, Vista Chemical Co.), alumina sol (Nalco ISH-614 TM, Nalco Chemical Co.), antimony oxide sol (Nalco ISH-611 TM, Nalco Chemical Co.), and alumina-coated silica sol (Nalco ISJ-613 TM, Nalco Chemical Company).

The term "solution" as used herein includes dispersions or suspensions of finely divided particles of ultramicroscopic size in a liquid medium. The solutions used in the practice of this invention are clear to milky in appearance.

The coating solution may also optionally contain a surfactant to improve wettability of the solution on the support, but inclusion of an excessive amount of surfactant may reduce the adhesion of the coating to the support. Examples of suitable surfactants preferably include nonionic surfactants such as trimethyl nonyl polyethylene glycol ether (Tergitol TMN-6 TM, Union Carbide Corp.) and octyphenoxy polyethoxy ethanol (Triton X-100 TM, Rohm and Haas Co.). Generally, the surfactant can be used in amounts of up to about 0.5 weight percent of the solution.

The coating solution may optionally contain a polymeric binder to aid in adhering the coating to the support. Useful polymeric binders include polyvinyl alcohol, polyvinyl acetate, polyesters, polyamides, polyvinyl pyrrolidone, copolyesters, copolymers of acrylic acid and/or methacrylic acid, and copolymers of styrene. The coating solution can contain up to about 20 weight percent of the polymeric binder based on the weight of the inorganic metal oxide particles. Useful amounts of polymeric binder are generally in the range of 1 to 15 weight percent.

Addition of various adjuvants, such as slip agents and processing oils, to the support material can be useful but may reduce the adhesion of the coating on the support.

Coating may be carried out by standard coating techniques such as bar coating, roll coating, curtain coating, spraying and dipping, or other techniques known to those in the art. The support may be treated prior to coating to obtain a uniform coating using techniques such as corona discharge, flame treatment, and electron beam. Generally, no pretreatment is required.

The thickness of the applied wet coating solution is dependent on the concentration of inorganic oxide particles in the coating solution and the desired thickness of the dried coating. The thickness of the wet coating solution is preferably such that the resulting dried coating thickness is from about 70 to 250 nm thick, more preferably about 100 to 200 nm thick.

After soaking a nonwoven web in the coating solution containing inorganic oxide particles the web is either dried at a moderately low temperature, generally less than about 200° C., preferably 80° to 120° C., or at room temperature, provided the drying time is sufficient to permit the coating to dry completely to provide good bonding of the oxides to the nonwoven webs. The drying temperature should be less than that at which the support degrades.

An alternative process for modifying the surface of woven or nonwoven webs is a plasma treatment. A plasma is generated by electrical discharge of the gas utilized between two flat electrodes, at a reduced pressure. Direct current (D.C.) or alternating current (A.C.) radiofrequencies or microwave plasmas can be useful, preferably at 10 to 125 kiloherz. Gas pressures of 10 mtorr to 10 torr can be used, preferably 0.5 to 2.0 torr. Power ranges preferably are 10 to 400 watts or power densities in the range of 0.05 to 2.25 w/cm$^2$.

Nonwoven or woven fibrous webs positioned between the two electrodes can be exposed to a plasm treatment for 1 second to 30 minutes, preferably 10 to 60 seconds.

Depending on the gas used, a plasma treatment provides the surface of the support with reactive, polar groups including hydroxy, ester, acid, carbonate, amine, peroxide, and hydroperoxide groups. These groups are a source of binding sites for the protein immobilizer compound.

The protein immobilizer coating is provided by deposition of any of the protein immobilizer polymers described above, preferably in a monolayer. The polymer is deposited onto the polar support from a dilute solution. Preferably the solution is an aqueous one. Generally, solutions containing 0.03 to 0.5 percent polymer (w/w) are used.

For example, the $\beta$-hydroxyalkyleneamine polymer can be deposited as a monolayer on the polarized surface of the support by immersing the support in a dilute aqueous solution of the polymer for 30 seconds to 24 hours, followed by a water wash. The support may be dried and stored or used immediately to contact an aqueous solution of the protein to be immobilized.

Deposition of the protein on the composite article, comprising a fibrous support which has been surface treated as described above and protein immobilizer compound, is preferably accomplished by immersion of the composite in the protein solution which preferably is a buffered aqueous solution. The optimum concentration of the protein solution will vary depending on the protein to be immobilized. Generally, protein solutions in the range of 0.01 to 100 mg/mL will be used. Following an equilibration period of a few seconds to 24 hours, the composite is removed from the protein and washed with water and/or buffer until unbound protein is removed. The resulting composite can then be dried in air and/or over a desiccant. In some cases, lyophilization can be used.

Objects and advantages of this invention are further illustrated by the following examples, but the particular materials and amounts thereof recited in these examples, as well as other conditions and details, should not be construed to unduly limit this invention.

The phosphate buffer used through the Examples, unless otherwise specified, was 0.01 M potassium dihydrogen phosphate, pH having been adjusted to 7.25 with 1N aqueous potassium hydroxide.

The catalase used throughout the Examples is commerically available catalase with activity (according to the manufacturer, Sigma Chemical Co.) of 40,000 International Units per milligram. However the activity was measured by a standard assay (described by Beers and Sizer, J. Biol. Chem. 195, 133 (1952)) wherein one unit of enzyme decomposed one micromole of hydrogen peroxide per minute at 15° C. at pH 7, to be 20,500 IU per milligram unless otherwise specified. All percents are by weight unless otherwise specified.

EXAMPLE 1

Polypropylene blown microfiber (BMF) was placed in a plasma treatment chamber that was equipped with two 23×33 cm (9×13 in.) substantially parallel aluminum electrodes. The material to be treated was placed on the non-driven electrode and the system evacuated to 10 millitorr. The system was then backfilled with 0.5 torr $CO_2$ as measured with a Vacuum General manometer monomer and a plasma ignited with a Plasmaloc TM generator (ENI, Inc.) with A.C. power at 25 KHz and at 200 watts. The plasma treatment was run for 0.5 min. After treatment the sample was brought to atmospheric pressure.

The trial was repeated using air, at 1.0 torr pressure, as the gas in the plasma treatment chamber.

Pads were cut from the treated BMF and were weighed and soaked 6 hours at room temperature in 0.05% DIMA solution. The pads were rinsed, drained, and soaked 16 hours at 4° C. in 0.1 mg catalase/ml in phosphate buffer. The measured free catalase activity was 48,000 unit/mg. The pads were soaked and rinsed until no free catalase was detected in the soaking solution.

The pads were soaked in 10 mL of 3% $H_2O_2$ solution and absorbance monitored at 240 nm as a function of time. The data are shown in TABLE I below.

TABLE I

| Plasma gas | Absorbance at 240 nm | | | | |
|---|---|---|---|---|---|
| | >15 sec. | 5 min. | 15 min. | 30 min. | 60 min. |
| $CO_2$ | >4.0 | 2.51 | 0.15 | 0.01 | 0.01 |
| air | >4.0 | 3.30 | 0.65 | 0.19 | 0.01 |

The data show that a plasma treatment can produce binding sites for protein immobilizers on BMF pads, and the pads are useful in the construction of the present invention.

EXAMPLE 2

Pads of nonwoven web of both an embossed and mat form of copolyester of 80/20 polyethylene terephthalate and polyethylene isophthalate, nylon 66, and thermally bonded polyethylene terephthalate (1.0 g each) were dipped in an amine stablized sol of silicon dioxide (Nalco 2326, Nalco Chemical Co., Oak Brook, IL) contianing 1.5% silicon dioxide in ethanol, then the pads were dried at 60° C. for about 15 minutes. The pads (see TABLE I below) were cut into pieces weighing 0.1 to 0.3 g, then soaked for six hours in 20 mL of 0.06% aqueous solution of the dimethylamine adduct of epoxidized polybutadiene (DIMA). The pads were drained, then rinsed with distilled water. The pads were soaked in 10 mL of an aqueous phosphatebuffered solution of 1 mg per mL of catalase for sixteen hours at 4° C. and at about 20° C. for 1.5 hours. The pads were soaked in buffer, drained and rinsed with distilled water until no catalase activity could be detected in the washings. A nonwoven polypropylene pad was prepared similarly, but the soaking time in DIMA solution was 16 hours and in catalase solution 24 hours. All of the drained pads were soaked in 10 mL of 0.2% hydrogen peroxide solution and the absorbance of the solution was measured initially and at intervals specified in TABLE II. The concentration of hydrogen peroxide in the second container of a two-container system was assumed to be about 0.2% when the volume of solution in the second container was 10 mL.

TABLE II

| Pad (weight in g) | Absorbance at 240 nm | | | | | |
|---|---|---|---|---|---|---|
| | 15 sec. | 1 min. | 5 min. | 15 min. | 30 min. | 60 min. |
| A. embossed copolyester (0.24 g) | 2.11 | 1.74 | 0.76 | 0.04 | 0.01 | — |

TABLE II-continued

| Pad (weight in g) | Absorbance at 240 nm | | | | | |
|---|---|---|---|---|---|---|
| | 15 sec. | 1 min. | 5 min. | 15 min. | 30 min. | 60 min. |
| B. embossed copolyester (0.24 g) | 2.08 | 1.57 | 0.56 | 0.5 | 0.01 | — |
| C. nylon 66 (0.14 g) | 0.82 | 0.62 | 0.05 | — | 0.03 | — |
| D. thermally bonded PET (0.14 g) | 1.72 | 0.92 | 0.21 | 0.07 | 0.02 | — |
| E. PET mat (0.13 g) | 1.83 | 1.80 | 0.97 | 0.28 | 0.14 | 0.02 |
| F. copolyester mat (0.14 g) | 1.74 | .18 | 0.69 | 0.15 | 0.11 | 0.02 |
| G. copolyester mat (0.12 g) | 1.97 | 1.45 | 0.61 | 0.10 | 0.09 | — |
| H. polypropylene (0.3 g) | 2.47 | — | 0.77 | 0.54 | 0.47 | — |

The data of TABLE II show the absorbance decreased from a maximum of 2.5 to a minimum range of 0.01 to 0.50 in 30 minutes. These values correspond to a decrease in hydrogen peroxide concentration from about 0.15% to less than 0.001%.

These data indicate the article of the invention is efficacious in removing hydrogen peroxide to a negligible concentration when used in a two-container system.

The soaked pads were then resoaked with 10 mL of 3% hydrogen peroxide solution and the aborbance of the solution at 240 nm was measured at various time intervals. The data are shown in TABLE III below.

TABLE III

| Pad | Absorbance at 240 nm | | | | | |
|---|---|---|---|---|---|---|
| | 15 sec. | 5 min. | 15 min. | 30 min. | 60 min. | 90 min. |
| A. embossed copolyester (0.24 g) | 3.12 | 0.05 | 0.05 | — | — | — |
| B. nylon 66 (0.14 g) | 0.45 | 0.05 | 0.05 | — | — | — |
| C. thermally bonded PET (0.14 g) | 3.10 | 0.12 | 0.11 | 0.12 | — | 0.12 |
| D. copolyester mat (0.13 g) | 3.15 | 2.99 | 3.02 | — | 3.17 | — |
| E. copolyester mat (0.12 g) | 3.05 | 0.24 | 0.10 | 0.07 | — | — |
| F. polypropylene (0.3 g) | 4.0 | 2.17 | 0.07 | 0.06 | — | — |

The data of TABLE III show that the articles used bound sufficient catalase to decompose 3% hydrogen peroxide and therefore that the article of the invention was efficacious in removing hydrogen peroxide to a negligible concentration when a one-container system was used.

EXAMPLE 3

The copolyester pad used in Example 2E, TABLE III, was placed in a 10 mL sample of 3% hydrogen peroxide in 0.01 M phosphate buffer, at pH 9.0, and the absorbance of the solution was measured at a wavelength of 240 nanometers at time intervals as shown in TABLE IV below. The pH of the solution was 10.0 after 90 min. and 8.7 after 16 hours.

The nylon pad of Example 2B and the copolyester pad of Example 2A were placed in 10 mL samples of 3% hydrogen peroxide in 0.01 M phosphate buffer, at pH 4.7, and the absorbance of the solution was measured at time intervals as shown in TABLE IV below. The pH of the solution containing the nylon pad was 6.2 and the solution containing the copolyester pad was 5.8, both measured after 90 minutes.

The pads were rinsed with phosphate buffer, pH 7.2, then drained and resoaked in 10 mL of 3% hydrogen peroxide in phosphate buffer, pH 7.4, and the absorbance at 240 nm was measured at time intervals as shown in TABLE IV.

The pH of the solutions containing the nylon and copolyester mats were 7.4 and 7.2, respectively, after 10 minutes of reaction.

TABLE IV

| Pad | Absorbance at 240 nm | | | | |
|---|---|---|---|---|---|
| | 45 sec. | 5 min. | 15 min. | 30 min. | 60 min. |
| A. copolyester mat. | | | | | |
| pH 9.0 | 3.15 | 0.19 | 0.17 | 0.16 | 0.14 |
| 7.4 | 3.15 | 3.07 | 3.09 | 3.07 | — |
| B. embossed polyester | | | | | |
| pH 4.7 | 3.14 | 0.07 | 0.11 | 0.11 | 0.09 |
| 7.4 | 3.14 | 1.4 | 0.22 | 0.05 | — |
| C. nylon mat | | | | | |
| pH 4.7 | 3.06 | 0.16 | 0.14 | 0.12 | 0.11 |
| 7.4 | 3.04 | 0.38 | 0.02 | 0.02 | — |

The data of TABLE IV show that the articles of the invention were efficacious under both acidic and basic conditions and remained useful even after cycling in an acidic solution of hydrogen peroxide.

EXAMPLE 4

A polypropylene pad weighing about 0.2 g containing catalase bonded to DIMA, prepared as described in Example 2, was refrigerated at 4° C. for one hour and then immersed in 10 mL of 3% hydrogen peroxide solution also at 4° C. The absorbances measured at less than 10 sec, 15 min, and 2½ hours were greater than 4, 0.09 and 0.04, respectively, indicating greater than 0.2%, 0.005% and 0.004% concentrations of hydrogen peroxide remaining, respectively.

This data of this Example show that the method of the invention works at relatively cold temperatures suitable for the storage of catalase.

EXAMPLE 5

An embossed polypropylene pad prepared according to the method of Example 2 was stored for two days at 4° C. in a desiccator. The pad was then soaked in 10 mL of buffer for 15 minutes at room temperature; the solution was decanted and the pad was immersed in 10 mL of 3% hydrogen peroxide solution and the absorbance was measured using the method of Example 1. For the pad stored dry, the average absorbance initially was greater than 4 and decreased to 0.009 at 60 minutes, corresponding to hydrogen peroxide concentrations of greater than 0.2% and less than 0.004%, respectively. The data showed that the article of the invention continued to function by decomposing hydrogen peroxide after being dried and rehydrated.

EXAMPLE 6

Pads of various nonwoven webs are described in Example 2 weighing 0.1 to 0.2 g were dipped in an amine stabilized sol of silicon dioxide (Nalco 2326, Nalco Chemical Company, Oak Brook, IL) containing 1.5% silicon dioxide in ethanol, then the pads were drained and dried at 60° C. for about 15 minutes. The dry pads were soaked for 24 hours, each pad in 10 mL of 0.5% of silane-treated polycarbodiimide in toluene at about 20° C. The pads were then rinsed with 20 mL of toluene, air dried in a fume hood for 16 hours and cured by heating for 15 minutes at 60° C. The pads were each soaked in 3 mL of 10 mg/mL solution of catalase for 4 hours at about 20° C., rinsed with distilled water and soaked in phosphate buffer (pH 7) for about 16 hours. The pads were rinsed again with distilled water and soaked in buffer for another 16 hours. No catalase activity was detected in the soaking solution. Each of the pads was then immersed in 10 mL of 0.2% hydrogen peroxide solution and the absorbance of the solution was measured at various time intervals using the method described in Example 1. The data are shown in Table V.

TABLE V

| Pad | Absorbance at 240 nm | | | | | |
|---|---|---|---|---|---|---|
| | 10 sec. | 5 min. | 15 min. | 30 min. | 60 min. | 90 min. |
| A. embossed copolyester (0.19 g) | 2.22 | 1.89 | 1.37 | 0.10 | 0.62 | 0.35 |
| B. embossed copolyester (0.16 g) | 2.36 | 2.07 | 1.55 | 1.04 | 0.72 | 0.60 |
| C. nylon 66 (0.07 g) | 2.04 | 2.03 | 1.50 | 1.23 | 0.94 | 0.82 |
| D. thermally bonded PET (0.08 g) | 2.31 | 1.90 | 1.29 | 0.76 | 0.77 | 0.29 |
| E. copolyester mat (0.11 g) | 1.98 | 1.76 | 1.38 | 1.04 | 0.67 | 0.67 |
| F. copolyester mat (0.09 g) | 2.04 | 1.60 | 0.98 | 0.80 | — | — |

These data show that the absorbance decreased to less than 1.0 in 60 minutes which correspond to a hydrogen peroxide concentration of less than 0.05%. The data also show that coupling agents other than DIMA are useful in the construction of the invention.

EXAMPLE 7

Pads of nonwoven webs of polypropylene and nylon 66 were soaked for 24 hours in about 25 mL of a 0.06% solution of the dimethylamine adduct of epoxidized polybutadiene at about 20° C. The pads were rinsed with distilled water. The pads were then soaked in 25 mL of a solution of catalase (1 mg per mL in 0.01 M phosphate buffer pH 7.2) for 3 hours at 4° C. and 2.5 hours at about 20° C. The pads were alternately soaked in buffer, drained and rinsed with distilled water overnight until no catalase activity could be detected in the washings.

A companion set of pads was prepared as controls in a similar manner but a ceramic-precursor gel layer was applied by dipping the nonwoven pads in 1.5% amine stabilized sol of silicon dioxide (Nalco 2326) at a ratio of about 0.1 g of silicon oxide to 1.25 g nonwoven fibers. The nylon and polypropylene pads were dried at about 60° C. for fifteen minutes. A 10 mL portion of 3% hydrogen peroxide in 0.01 M phosphate buffer, pH 7.2, was added to each pad and the decomposition of hydrogen peroxide was monitored by recording the absorbance of the solution at 240 nm at time intervals up to at least thirty minutes. The data was shown in TABLE VI (A-D). The nylon pads were soaked for about 65 hours with 2 buffer changes, then drained and resoaked in 10 mL of 3% H$_2$O$_2$. The decomposition was monitored as stated above. See TABLE VI (E and F).

TABLE VI

| Pads (all with DIMA) | Weight | Absorbance at 240 nm | | | | |
|---|---|---|---|---|---|---|
| | | 15 sec. | 1 min. | 5 min. | 15 min. | 30 min. |
| A. polypropylene + SiO$_2$ | 0.10 | >4 | >4 | 1.97 | 0.91 | 0.24 |
| B. polypropylene, no SiO$_2$ | 0.18 | >4 | >4 | >4 | >4 | >4 |
| C. nylon 66 + SiO$_2$ | 0.10 | >4 | 0.82 | 0.22 | 0.10 | 0.04 |
| D. nylon 66, no SiO$_2$ | 0.12 | >4 | >4 | — | — | — |
| E. nylon 66 + SiO$_2$ | 0.10 | — | 3.20 | 2.81 | 1.80 | 0.09 |
| F. nylon 66, no SiO$_2$ | 0.12 | — | 3.17 | 3.19 | — | 3.15 |

The data of TABLE VI show that a polypropylene pad without a gel coating showed no detectable enzymatic activity within thirty minutes, and the nylon pad without a gel coating showed reduced enzymatic activity within thirty minutes.

EXAMPLE 8

Embossed copolyester (80% polyethylene terephthalate, 20% polyethylene isophthalate) nonwoven pads were prepared as in Example 7 with no DIMA coating. A companion copolyester pad was prepared with DIMA as a control. The addition and decomposition of 3% hydrogen peroxide solution was effected as disclosed in Example 7. The data was shown in TABLE VII.

TABLE VII

| Pads with SiO$_2$ | Absorbance at 240 nm | | | | |
|---|---|---|---|---|---|
| | 15 sec. | 1 min. | 5 min. | 15 min. | 30 min. |
| embossed copolyester, with DIMA (3.5 × 3.5 cm) | >4 | 3.20 | 3.07 | 0.78 | 0.45 |
| embossed copolyester, no DIMA (3.5 × 3.5 cm) | >4 | 3.26 | 3.37 | 3.15 | 3.13 |

The data of TABLE VII show a significant increase in catalase activity bound to the fibrous web when the DIMA coating is used.

EXAMPLE 9

A cellulose pad (No. 2 Whatman filter paper) and woven nylon were coated with silicon dioxide, DIMA, and catalase as described in Example 7.

A pad of alumina-boria-silica 3:1:2 ceramic fiber (Nextel 312 TM, 3M, St. Paul, MN) was coated with DIMA and catalase as described above in Example 7. A 10 mL aliquot of 3% hydrogen peroxide solution was added to each pad and the absorbance of the solution at 240 nm was monitored. The absorbance data are shown in TABLE VII below.

TABLE VIII

| | Weight (in g) | Absorbance at 240 nm | | | |
|---|---|---|---|---|---|
| | | 1 min. | 5 min | 15 min | 30 min. |
| cellulose | 0.65 | 3.18 | 0.22 | 0.20 | 0.22 |
| woven Nylon | 0.64 | >4 | 0.57 | 0.71 | 0.17 |
| Nextel 312 | 1.36 | >4 | 1.03 | — | 0.11 |

The data of TABLE VIII for absorbance show detectable bound catalase when evaluated in 10 mL of 3% hydrogen peroxide demonstrating that supports other than nonwovens can be used in this construction.

EXAMPLE 10

Catalase was bound to a nonwoven polyethylene terephthalate pad which was provided with DIMA and gel coatings as described in Example 2. Pads were sterilized with ethylene oxide at 29° C. and degassed at 4° C. for several days.

Ten polyvinylpyrrolidone/HEMA lenses (Softcon TM American Optical, 55% water content soft contact lenses) were inoculated with sixty five million *Pseudomonas aeruginosa* (American Type Culture Collection, ATCC,#27853) colony forming units (cfu).

Two lenses were cleaned with Bausch and Lomb TM Daily Cleaner TM and microorganisms were eluted with 5% Tween-80 TM saline solution and plated on tryptic soy agar. About eight thousand cfu's of the *Pseudomonas aeruginosa* were present on the lenses before hydrogen peroxide disinfection.

Eight of the ten lenses were cleaned with Bausch and Lomb Daily Cleaner and rinsed with sterile saline and placed in lens holders.

In a two-container, two-step system, a lens was inserted into each of two containers containing 10 mL of 3% hydrogen peroxide, in 0.01 M phosphate buffer, pH 7.2, for 10 minutes, removed and reinserted into containers containing 10 mL of phosphate buffer. A 0.13 g pad of polyester with immobilized catalase as prepared in Example 2 was inserted with the lens which was soaked for four hours.

In a one container, one-step system, a lens was inserted into each of two containers containing 10 mL of 3% hydrogen peroxide in phosphate buffer with 0.15 g pads containing catalase and soaked for 4 hours.

Two lenses were disinfected and neutralized as recommended by the manufacturer in two Septicon T-M Catalytic Disinfection Systems. This system requires soaking lenses in about 10 mL of Lensept TM (3% $H_2O_2$) solution for ten minutes, removal, and reinsertion in a second container with about 10 mL of Sensitive Eyes TM saline solution (Bausch & Lomb) and a platinum coated disc for four hours.

Two lenses were placed in 10 mL of sterile saline for four hours.

The eight lenses were removed from the disinfection containers, then placed in 10 mL tryptic soy broth and incubated at 35° C. for 6 days. The final soaking solutions were transferred to 100 mL of broth and incubated for 6 days at 35° C. At the end of the 6-day incubation, containers of broth were scored for the presence of visible turbidity in the solutions. Visible turbidity in the incubated broth indicated lack of disinfection (+). The results are shown in Table IX below.

TABLE IX

| Sample | System | Lens | Soak solution |
|---|---|---|---|
| 1 | 2-step, 2-container catalase | − | − |
| 2 | 2-step, 2-container catalase | − | − |
| 3 | 1-step, 1-container catalase | − | − |
| 4 | 1-step, 1-container catalase | − | − |
| 5 | Septicon | − | + |
| 6 | Septicon | − | − |
| 7 | saline only | + | + |
| 8 | saline only | − | + |

In TABLE IX the data show that one lens without hydrogen peroxide disinfection was not disinfected. The saline soaks from both of these lenses showed microbial growth. The Sensitive Eyes soaking solution from one of the Septicon systems also was not disinfected. The catalase one-step and two-step systems both resulted in disinfected lenses and the soak solutions show no microbial growth.

The data of Table IX show the method of the invention can be used in a one-step, one-container system, and also in a two-step, two-container system.

Various modifications and alterations of this invention will become apparent to those skilled in the art without departing from the scope and spirit of this invention and it should be understood that this invention is not to be unduly limited to the illustrative embodiments set forth herein.

We claim:

1. A composite article comprising in sequence:
   (a) a polymeric fibrous support having a large surface area, which surface has been subjected to a surface plasma treatment carried out at a frequency of 10 to 125 kiloherz with a power density in the range of 0.05 to 2.25 w/cm$^2$ generated between two electrodes in a gas at a pressure in the range of 10 mtorr to 10 torr to provide a polar surface having binding sites thereon,
   (b) a layer of a protein immobilizer compound comprising a polymer or a silane-functional compound adhering to the resulting treated surface and capable of immobilizing enzymes, and
   (c) an enzyme bound to said layer of protein immobilzer compound.

2. The article according to claim 1 wherein said plasma treatment utilizes a gas selected from the group consisting of air, oxygen, carbon dioxide, argon, helium, nitrous oxide, or water vapor.

3. The article according to claim 1 wherein said gas is air or carbon dioxide.

4. The article according to claim 1 wherein said support is woven or nonwoven.

5. The article according to claim 1 wherein said support is polyalkylene, polyvinyl chloride, polyamide, polyvinyl alcohol, polystyrene, polyacrylsulfone, polyester, polycarbonate, polyacrylate, cellulosic, polyurethane, or combinations thereof.

6. The article according to claim 1 wherein said polymer is a beta-hydroxyalkyleneamine-containing polymer, and the silane-functional compound is a silane-treated polycarbodiimide polymer.

7. The article according to claim 6 wherein said polymer is an amine adduct of epoxidized poly-cis-1,4-butadiene, epoxidized styrene/cis-1,4-butadiene, or polyglycidyl methacrylate.

8. The article according to claim 7 wherein said amine is dimethylamine, diethylamine, morpholine, piperidine, or n-propylamine.

9. The article according to claim 1 wherein said enzyme is urease, glucose oxidase, invertase, peroxidase, catalase, papain, lipase, cellulase, dextranase, amylase, ribonuclease, carboxypeptidase or urokinase.

* * * * *

UNITED STATES PATENT AND TRADEMARK OFFICE
CERTIFICATE OF CORRECTION

PATENT NO. : 4,855,234
DATED : August 8, 1989
INVENTOR(S) : Hendrickson et al.

It is certified that error appears in the above-identified patent and that said Letters Patent is hereby corrected as shown below:

Col. 5, line 62, "in" should read --an--.
Col. 8, line 1, "Oal" should read --Oak--.
Col. 8, line 4, "ISH-" should read -- ISJ- --.
Col. 8, line 6, "ISH-" should read --ISJ- --.
Col. 8, line 38, "on" should read --to--.
Col. 9, line 5, "plasm" should read --plasma--.
Col. 9, line 48, "through" should read "throughout--.
Col. 10, line 40, "contianing" should read --containing--.

Signed and Sealed this

Twenty-second Day of October, 1991

Attest:

HARRY F. MANBECK, JR.

Attesting Officer

Commissioner of Patents and Trademarks